United States Patent [19]

Takashima et al.

[11] Patent Number: 5,563,053
[45] Date of Patent: Oct. 8, 1996

[54] PROCESS FOR PRODUCTION OF AMIDE COMPOUNDS USING MICROORGANISM

[75] Inventors: Yoshiki Takashima, Ashiya; Fujio Mukumoto; Satoshi Mitsuda, both of Takarazuka, all of Japan

[73] Assignee: Sumitomo Chemical Company, Limited, Osaka-fu, Japan

[21] Appl. No.: 382,152

[22] Filed: Feb. 1, 1995

[30] Foreign Application Priority Data

Feb. 1, 1994 [JP] Japan .................................. 6-010518

[51] Int. Cl.$^6$ ............................. C12P 13/02; C12P 17/12
[52] U.S. Cl. ........................................... 435/122; 435/129
[58] Field of Search ..................................... 435/129, 122

[56] References Cited

U.S. PATENT DOCUMENTS

| | | | |
|---|---|---|---|
| 4,001,081 | 1/1977 | Commeyras et al. | 435/129 |
| 4,248,968 | 2/1981 | Watanabe et al. | 435/129 |
| 4,555,487 | 11/1985 | Yamada et al. | 435/129 |
| 4,637,982 | 1/1987 | Yamada et al. | 435/129 |
| 4,908,313 | 3/1990 | Satoh et al. | 435/129 |
| 5,089,411 | 2/1992 | Yamada et al. | 435/129 |
| 5,200,331 | 4/1993 | Kawakami et al. | 435/129 |
| 5,314,819 | 5/1994 | Yamada et al. | 435/129 |
| 5,318,908 | 6/1994 | Seki et al. | 435/129 |
| 5,334,519 | 8/1994 | Yamada et al. | 435/129 |
| 5,395,758 | 3/1995 | Takashima et al. | 435/129 |

FOREIGN PATENT DOCUMENTS

| | | |
|---|---|---|
| 0188316 | 7/1988 | European Pat. Off. |
| 0486289 | 5/1992 | European Pat. Off. |
| 0530522 | 3/1993 | European Pat. Off. |
| 64-86889 | 3/1989 | Japan . |
| 2054563 | 2/1981 | United Kingdom . |

OTHER PUBLICATIONS

Nakamura et al., Intl. J. of Systematic Bacteriology, vol. 38, No. 1, pp. 63–73 (Jan. 1988).
Database WPI, Section Ch., Week 9226, Derwent Pub., Ltd., London, GB; Class B05, AN 92–214132 (Abstract) and JP-A-04 144 697, May 1992 (Abstract).

Primary Examiner—Herbert J. Lilling
Attorney, Agent, or Firm—Birch, Stewart, Kolasch & Birch, LLP

[57] ABSTRACT

The present invention provides a process for production of amide compounds, which includes converting a nitrile compound into its corresponding amide compound by hydrating the nitrile compound in the presence of a cultured broth of bacterial cells, intact bacterial cells, disrupted bacterial cells or enzymes contained therein, or immobilized preparations obtainable by immobilizing intact bacterial cells, disrupted bacterial cells or enzymes contained therein, the bacterial cells being those of a biologically pure culture of a thermophilic microorganism having hydration activity to convert a nitrile compound into its corresponding amide compound, such as *Bacillus smithii* SC-J05-1 (FERM BP-4935).

9 Claims, No Drawings

PROCESS FOR PRODUCTION OF AMIDE COMPOUNDS USING MICROORGANISM

FIELD OF THE INVENTION

The present invention relates to a process for production of amide compounds using a microorganism having hydration activity to convert a nitrile compound into its corresponding amide compound.

BACKGROUND OF THE INVENTION

In recent years, biological catalysts such as microorganisms have been widely used for chemical reactions. For example, it is well known that nitriles compounds can be converted into amide compounds by hydration using a certain strain of the genus Bacillus, Bacteridium, Micrococcus or Brevibacterium (U.S. Pat. No. 4,001,081); Corynebacterium or Nocardia (U.S. Pat. No. 4,248,968); Pseudomonas (U.S. Pat. No. 4,555,487); Rhodococcus or Microbacterium (EP-188,316); or Fusarium (JP-A 64-86889/1989).

All of these microorganisms, however, fall under the category of mesophilic bacteria which cannot grow at a temperature of 55° C. or higher.

In addition, the hydration activity of mesophilic bacteria to convert a nitrile compound into its corresponding amide compound are not stable in the range of temperature of higher than room temperature. For this reason, the production of amide compounds using such mesophilic bacteria is usually conducted at lower temperatures. In this case, cooling facilities are required for keeping the reactor at lower temperatures and high quantity of energy is consumed for the cooling, which lead to a remarkable increase in the production cost.

SUMMARY OF THE INVENTION

Under these circumstances, the present inventors have extensively searched for microorganisms having hydration activity to convert a nitrile compound into its corresponding amide compound even in the range of temperature higher than room temperature. As a result, they have found that a thermophilic microorganism isolated from soil of a certain hot spring in Okayama-ken complies with such requirements, thereby completing the present invention.

Thus, the present invention provides a process for production of amide compounds, which comprises converting a nitrile compound into its corresponding amide compound by hydrating the nitrile compound in the presence of a cultured broth of bacterial cells, intact bacterial cells, disrupted bacterial cells or enzymes contained therein, or immobilized preparations obtainable by immobilizing intact bacterial cells, disrupted bacterial cells or enzymes contained therein, the bacterial cells being cells of a biologically pure culture of a thermophilic microorganism having hydration activity to convert a nitrile compound into its corresponding amide compound.

The present invention also provides a biologically pure culture of a novel thermophilic microorganism having hydration activity to convert a nitrile compound into its corresponding amide compound, which is designated *Bacillus smithii* SC-J05-1 (FERM BP-4935).

DETAILED DESCRIPTION OF THE INVENTION

According to the process of the present invention, various nitrile compounds can be converted into their corresponding amide compounds. Examples of the nitrile compound are aliphatic nitriles such as n-butyronitrile, n-valeronitrile, isobutyronitrile, acetonitrile and pivalonitrile; halogen-containing nitrile compounds such as 2-chloropropionitrile; unsaturated aliphatic nitrile compounds such as acrylonitrile, crotononitrile and methacrylonitrile; hydroxynitrile compounds such as lactonitrile and mandelonitrile; aminonitrile compounds such as 2-phenylglycinonitrile; aromatic nitrile compounds such as benzonitrile and cyanopyridines; and dinitrile compounds such as malononitrile, succinonitrile and adiponitrile. Preferred are n-butyronitrile, n-valeronitrile, isobutyronitrile, acetonitrile, pivalonitrile, 2-chloropropionitrile, acrylonitrile, crotononitrile, methacrylonitrile, benzonitrile, 2-cyanopyridine, 3-cyanopyridine, 4-cyanopyridine, malononitrile, succinonitrile and adiponitrile.

The conversion of a nitrile compound into an amide compound is achieved by hydrating the nitrile compound in the presence of a cultured broth of bacterial cells, intact bacterial cells, disrupted bacterial cells or enzymes contained therein, or immobilized preparations obtainable by immobilizing intact bacterial cells, disrupted bacterial cells or enzymes contained therein. The bacterial cells are those of a biologically pure culture of a thermophilic microorganism having hydration activity to convert a nitrile compound into its corresponding amide compound.

The microorganism to be used in the present invention is not particularly limited, so long as it falls under the category of thermophilic microorganisms having hydration activity to convert a nitrile compound into its corresponding amide compound. As used herein, the term "thermophilic microorganism" refers to a microorganism having ability to grow even at an incubation temperature of 55° C. or higher.

For example, the desired microorganism can be obtained by the following procedures. First, soil is collected in the nature, and the collected soil or a supernatant obtained after the soil is thoroughly suspended in water, is added at an appropriate amount to a well-known culture medium for growth of microorganisms, for example, a liquid medium or an agar medium containing glycerol, polypeptone, yeast extract and malt extract as main ingredients, followed by incubation at a temperature of 55° C. or higher for a period of from about 24 hours to about 3 months. The cultured broth obtained in this way or a part of the bacterial cells isolated were spread on an agar plate medium containing the same ingredients as described above, followed by further incubation to form some colonies, from which a thermophilic microorganism can be isolated.

The thermophilic microorganisms thus obtained from the nature or deposited in various microorganism depository organizations are allowed to grow by incubation in a test tube or a flask, having a liquid medium containing the above medium ingredients and a nitrile compound or an amide compound, such as isovaleronitrile, crotononitrile or crotonamide, at a temperature of 55° C. or higher for an appropriate period of time, for example, from about 12 hours to about 7 days. The cultured broth is added to an aqueous solution of a nitrile compound such as propionitrile or acrylonitrile, and the reaction is effected, for example, at a temperature of 30° C. for a period of from about 10 to about 60 minutes. Then, the reaction mixture is examined whether an amide compound was produced or not, which makes it possible to readily find a thermophilic microorganism having hydration activity to convert a nitrile compound into its corresponding amide compound. For the detection of amide compounds, an analysis method by gas chromatography as described below can be employed, for example.

As a typical example, *Bacillus smithii* SC-J05-1 can be used in the process of the present invention. This bacterial strain is a thermophilic microorganism of the genus Bacillus, which was found by the present inventors to have higher activity to hydrate the nitrile groups of nitrile compounds and deposited with the National Institute of Bioscience and Human Technology in the Agency of Industrial Science and Technology, Japan, under the accession number of FERM P-14037 on Dec. 24, 1993, which has been transferred to the International Deposit under the Budapest Treaty under the accession number of FERM BP-4935 on Dec. 14, 1994.

The bacteriological characteristics of *Bacillus smithii* SC-J05-1 are as follows:

(a) Morphology:
   1. Shape and size of cells
      Shape: rods
      Size: 0.5–0.8 μm × 0.8–2 μm
   2. Polymorphism: none
   3. Motility: active, peritrichous flagella
   4. Sporulation: found
   5. Gram staining: variable
   6. Acid fastness: none
(b) Growth properties:
   1. Nutrient agar plate culture: round, convex, non-glossy, pale brown
   2. Nutrient agar slant culture: non-glossy, pale brown
   3. Nutrient broth liquid culture: uniformly turbid growth
   4. Nutrient broth gelatin stab culture: not liquefied
   5. Litmus milk: not changed
(c) Physiological properties:
   1. Nitrate reduction: −
   2. Denitrification: −
   3. MR test: +
   4. VP test: −
   5. Indole formation: −
   6. Hydrogen sulfide formation: +
   7. Starch hydrolysis: −
   8. Citrate utilization
      Koser medium: ±
   9. Inorganic nitrogen source utilization
      $NaNO_3$: −
      $(NH_4)_2SO_4$: +
   10. Pigment formation
      King's A medium: −
      King's B medium: −
   11. Urease: −
   12. Oxidase: +
   13. Catalase: − to ±
   14. Growth conditions
      pH: 4.1–7.5
      Temp.: 30–60° C.
   15. Attitude to oxygen: slightly aerobic
   16. O—F test: F
   17. Acid and gas formation from sugar

| | Acid | Gas |
|---|---|---|
| L-Arabinose: | − | − |
| D-Xylose: | + | − |
| D-Glucose: | + | − |
| D-Mannose: | + | − |
| D-Fructose: | + | − |
| D-Galactose: | + | − |
| Maltese: | + | − |
| Sucrose: | + | − |
| Lactose: | − | − |
| Trehalose: | + | − |
| D-Sorbitol: | − | − |
| D-Mannitol: | + | − |
| Inositol: | + | − |
| Glycerol: | + | − |
| Starch: | − | − |

(d) Other properties:
   1. Mol % G + C of DNA: 40.6%

An extensive search was made for the literature of a microorganism exhibiting the above characteristics, and it has been reported by L. K. Nakamura et at., *International Journal of Systematic Bacteriology*, 38, 63–73 (1988) that *Bacillus smithii* exhibits the same characteristics as described above. From these results, the bacterial strain SC-J05-1 found by the present inventors was identified as one strain belonging to *Bacillus smithii*.

No knowledge has been obtained that microorganisms of *Bacillus smithii* have hydration activity to convert a nitrile compound into its corresponding amide compound. In this respect, it is considered that *Bacillus smithii* SC-J05-1 (FERM BP- 4935) is a novel bacterial strain. Further, variants of the bacterial strain, i.e., mutants, cell fusion strains or recombinant strains derived from *Bacillus smithii* SC-J05-1 (FERM BP-4935), can also be used in the process of the present invention.

A culture of the microorganism for use in the process of the present invention can be prepared in various kinds of media containing carbon and nitrogen sources, organic and/ or inorganic salts, and the like, all of which have been widely used for preparing a culture of ordinary bacteria.

Examples of the carbon sources are glucose, glycerol, dextrin, sucrose, organic acids, animal and vegetable oils, and molasses.

Examples of the nitrogen source are organic and inorganic nitrogen sources such as broth, peptone, yeast extract, malt extract, soy bean powder, corn steep liquor, cotton seed powder, dry yeast, casamino acid, sodium nitrate and urea.

Examples of the organic and inorganic salts are chlorides, sulfates, acetates, carbonates and phosphates of elements such as potassium, sodium, magnesium, iron, manganese, cobalt and zinc. Specific examples thereof are potassium chloride, sodium chloride, magnesium sulfate, ferrous sulfate, manganese sulfate, cobalt chloride, zinc sulfate, copper sulfate, sodium acetate, calcium carbonate, sodium carbonate, potassium monohydrogenphosphate, potassium dihydrogenphosphate, sodium monohydrogenphosphate and sodium dihydrogenphosphate.

In the process of the present invention, it is preferred that a nitrile compound such as isovaleronitrile and crotononitrile or an amide compound such as crotonamide is added to the culture medium for the purpose of enhancing the nitrile-hydration activity of the microorganism used therein. For example, these compounds may be used at an amount of from about 10 mg to about 1 g per 100 mL of the culture medium.

A culture of the microorganism used in the process of the present invention is prepared according to conventional procedures employed for ordinary bacteria, in the form of either a solid culture or a liquid culture such as shaking culture using test tubes, reciprocating shakers or rotary shakers, and other cultures using jar fermenters or fermentation tanks.

A culture of the microorganism is usually incubated under aerobic conditions. In particular, when a jar fermenter is used, it is necessary to introduce aseptic air thereinto, usually at a rate of from about 0.1 to about 2 times the culture volume per minute.

The incubation temperature may vary within a range in which the microorganism used is viable in culture. For example, the culture is incubated at a temperature of from about 30° C. to about 100° C. The medium pH is controlled, for example, at from about 2 to about 11.

In particular, when a microorganism of *Bacillus smithii* is cultivated, the incubation temperature is in the range of from about 30° C. to about 100° C., preferably from about 40° C. to about 55° C., and the medium pH is in the range of from about 5 to about 7.

The incubation period may vary depending upon various conditions, and the culture is usually incubated over a period of from about 1 to about 7 days.

The process of the present invention is conducted, for example, as follows.

The cultured broth of bacterial cells, intact bacterial cells, or the materials obtainable by treating the bacterial cells of a microorganism prepared in the manner as described above are suspended in water or an aqueous solution such as a phosphate buffer, and this suspension is added to a nitrile compound for reaction.

As used herein, the term "materials obtainable by treating bacterial cells" refers to disrupted bacterial cells or enzymes contained therein, obtained by a conventional technique such as ultrasonic disintegration, homogenization or disruption with a French press, or referred to immobilized preparations obtainable by immobilizing intact or disrupted bacterial cells, or enzymes contained therein, in a readily removable state after their insolubilization, according to an immobilization method such as a carrier-supporting method in which these materials are supported on an appropriate carrier through covalent linkage, ionic bonding, adsorption or the like, or an inclusion method in which these materials are included in the network structure of a polymer.

The bacterial cells or the materials obtainable by treating the bacterial cells are usually used at a concentration of from about 0.01 to about 20 wt %, preferably from about 0.01 to about 10 wt %. In the case of enzymes or immobilized preparations, the concentration thereof may vary depending upon their purity or immobilization method used; for example, it is preferred that the enzymes and immobilized preparation are prepared so as to have similar activity to hydrate nitrile groups to that of the bacterial cells or the material obtainable by treating the bacterial cells. The cultured broth of the bacterial cells may be used without any further treatment before addition of a nitrile compound. It is preferred that the cultured broth of the bacterial cells is diluted or concentrated so as to have similar activity to hydrate nitrile groups to that of the bacterial cells or the material of obtainable by treating the bacterial cells.

The reaction is usually effected at a temperature of from about 0° to about 70° C., preferably from about 0° to about 50° C., at a pH of from about 5 to about 10, preferably from about 6 to about 9, for a period of from about 10 minutes to about 72 hours. When the pH is controlled within the above range, the bacterial cells can accumulate the produced amide compound into the reaction mixture at high concentrations.

The amide compound thus produced can be recovered from the reaction mixture by any conventional method known in the art. For example, the bacterial cells or the materials obtainable by treating the bacterial cells are separated from the reaction mixture by centrifugation, followed by treatment with activated charcoal or an ion exchange resin to remove impurities. The purified mixture is concentrated by distillation or evaporation under reduced pressure, and the precipitated crystals are recrystallized from an organic solvent such as methanol to give the desired amide compound.

The present invention will be further illustrated by the following Examples which are not to be construed to limit the scope thereof.

EXAMPLE 1

Isolation of Bacterial Cells

At a certain hot spring in Okayama-ken, soil was collected, and the collected soil was added to a culture medium (pH 7.2) containing 1.0 wt % glycerol, 0.5 wt % polypeptone, 0.3 wt % yeast extract and 0.3 wt % malt extract, followed by incubation at 55° C. with reciprocating shaking for 21 days. A part of the cultured broth was spread on an agar medium containing the same ingredients as described above, and the culture was incubated to form some colonies.

From these colonies, bacterial cells were isolated, and a loopful of the isolated bacterial cells were inoculated into a liquid medium containing 0.1 wt % isovaleronitrile in addition to the same ingredients as described above, followed by incubation at 55° C. for 24 hours, which afforded a cultured broth as a specimen. Then, 1 mL of the cultured broth was added to 9 mL of 2.78 wt % acrylonitrile solution in 0.05M phosphate buffer, pH 7.7, and the reaction was initiated at 10° C. After 10 minutes, 1 mL of 2N HCl was added for stopping the reaction. An aliquot of the reaction mixture was taken and analyzed by gas chromatography to examine the presence of acrylamide produced for screening some bacterial strain having activity to hydrate nitrile groups. In this way, Bacillus smithii SC-J05-1 was obtained as a thermophilic microorganism having hydration activity to convert a nitrile compound into its corresponding amide compound.

Conditions for Gas Chromatography

Column: packed column
    Carrier: Porapak type Q (mesh 80–100)
    Length: 1.1 m Column Temperature: 210° C.

Flow Rate of Carrier Gas: 50 mL/min.

Injection Volume of Sample: 2 μL

EXAMPLE 2

Culture of Bacterial Cells for Examination of Thermophilic Properties

The bacterial cells of Bacillus smithii SC-J05-1 obtained in Example 1 and the bacterial cells of Bacillus sp. bacteria (deposited in the genetics laboratory collection, École Nationale Supérieure des Agriculture, French, under the storage number of R332 and also deposited in the National Institute of Bioscience and Human-Technology in the Agency of Industrial Science and Technology, Japan, under the accession number of FERM P-2717; hereinafter referred to as Bacillus sp. bacteria R332) which is a mesophilic bacteria as described in JP-B 62-21519/1987 were independently spread on a nutrient agar plate medium, and incubated at different temperatures to examine the ability to grow. The results are shown in Table 1.

TABLE 1

| Incubation temperature for each bacterial strain (°C.) | Bacillus smithii SC-J05-1 (present invention) | Bacillus sp. bacteria R332 (control) |
| --- | --- | --- |
| 20 | − | ++ |
| 30 | + | ++ |
| 40 | ++ | + |
| 55 | ++ | − |
| 60 | ++ | − |
| 70 | − | − |

Criteria:
(−) not grown;
(+) grown; and
(++) greatly grown

As can be seen from Table 1, *Bacillus smithii* SC-J05-1 of the present invention was a different thermophilic microorganism from Bacillus sp. bacteria R332 as the control.

EXAMPLE 3

Culture of Bacterial Cells

In a 500 mL Sakaguchi flask was placed 100 mL of a sterilized culture medium (pH 7.2) containing 1.0 wt % sucrose, 0.5 wt % polypeptone, 0.3 wt % yeast extract, 0.3 wt % malt extract, 0.001 wt % ferrous sulfate, 0.001 wt % manganese sulfate, 0.001 wt % cobalt chloride and 0.001 wt % zinc sulfate. This flask was inoculated with 0.1 mL of a cultured broth of *Bacillus smithii* SC-J05-1 which had been cultivated on the same culture medium as described above. This flask was then incubated at 55° C. with reciprocal shaking at a rate of 135 strokes/min. for 1 day, which afforded a cultured broth of bacterial cells of *Bacillus smithii* SC-J05-1.

REFERENCE EXAMPLE 1

Culture of Bacterial Cells

In a 500 mL Sakaguchi flask was placed 100 mL of a sterilized culture medium (pH 7.2) containing 1.0 wt % glycerol, 0.5 wt % polypeptone, 0.3 wt % yeast extract, 0.3 wt % malt extract, 0.001 wt % ferrous sulfate, 0.001 wt % manganese sulfate, 0.001 wt % cobalt chloride and 0.001 wt % zinc sulfate. This flask was inoculated with 0.1 mL of a cultured broth of Bacillus sp. bacteria R332 which had been cultivated on the same culture medium as described above. This flask was then incubated at 30° C. with reciprocal shaking at a rate of 135 strokes/min. for 2 days, which afforded a cultured broth of bacterial cells of Bacillus sp. bacteria R332.

COMPARATIVE EXAMPLE 1

Thermostability

From 400 mL of the cultured broth of bacterial cells of *Bacillus smithii* SC-J05-1 obtained in Example 3, the bacterial cells were collected by centrifugation at 10,000×g for 10 minutes. After washing with 0.05M phosphate buffer, pH 7.7, these bacterial cells were suspended in 100 mL of the same buffer. The suspension of bacterial cells thus prepared was examined for hydration activity to convert a nitrile compound into its corresponding amide compound. Further, to examine the thermostability of the activity, the same suspension of bacterial cells was kept at a constant temperature for a constant period of time.

The hydration activity to convert a nitrile compound into its corresponding amide compound was measured by the following procedures. To 9 mL of 2.78% acrylonitrile solution in 0.05M phosphate buffer, pH 7.7, was added 1 mL of a tested solution, and the reaction was initiated at 10° C. After 10 minutes, 1 mL of 2N HCl was added for stopping the reaction. An aliquot of the reaction mixture was taken and analyzed by gas chromatography under the same conditions as described in Example 1 to determine the amount of acrylamide produced.

With respect to the unit of enzyme activity as used hereinafter, the activity to convert 1 μmol of acrylonitrile into acrylamide per minute was defined as one unit (U).

Then, from 400 mL of the cultured broth of bacterial cells of Bacillus sp. bacteria R332 obtained in Reference Example 1, the bacterial cells were collected by centrifugation at 10,000×g for 10 minutes. After washing with 0.05M phosphate buffer, pH 7.7, these bacterial cells were suspended in 10 mL of the same buffer. The suspension of bacterial cells thus prepared was examined for the hydration activity to convert a nitrile compound into its corresponding amide compound in the same manner as described above. Further, to determine the thermostability of the activity, the same suspension of bacterial cells was kept at a constant temperature for a constant period of time, and then examined for the activity. The activity was measured in the same manner as described above. Based on the results of the measurement, the activity after the treatment relative to the activity before the treatment (hereinafter referred to as remaining activity) was calculated for each bacterial strain, and the remaining activity of *Bacillus smithii* SC-J05-1 was converted on the basis of the remaining activity of Bacillus sp. bacteria R332 being set to be 100.

TABLE 2

| Treatment temperature (°C.) | Treatment period (hr) | *Bacillus smithii* SC-J05-1 | Bacillus sp. bacteria R332 |
| --- | --- | --- | --- |
| 50 | 0.5 | 6542 | 100 |
| 40 | 1.5 | 280 | 100 |
| 30 | 47 | 212 | 100 |
|  |  | (present invention) | (control) |

COMPARATIVE EXAMPLE 2

Reaction Stability

From the cultured broth of bacterial cells of *Bacillus smithii* SC-J05-1 obtained in Example 3, the bacterial cells were collected by centrifugation at 10,000×g for 10 minutes. After washing with 0.05M phosphate buffer, pH 7.7, these bacterial cells were suspended in the same buffer to give a 20 U/mL bacterial cell suspension.

On the other hand, from the cultured broth of bacterial cells of Bacillus sp. bacteria R332, the bacterial cells were collected by centrifugation at 10,000×g for 10 minutes. After washing with 0.05M phosphate buffer, pH 7.7, these bacterial cells were suspended in 100 mL of the same buffer to give 20 U/mL of the bacterial cell suspension.

Then, 1 mL of each of the bacterial cell suspension and 9 mL of 2.78 wt % acrylonitrile solution in 0.05M phosphate buffer, pH 7.7, were mixed together, and the reaction was effected at 30° C., 40° C., 50° C. or 60° C. After ten minutes, 1 mL of 2N HCl was added for stopping the reaction. An aliquot of the reaction mixture was taken and analyzed by gas chromatography under the same conditions as described in Example 1 to determine the amount of acrylamide produced. The amounts of acrylamide produced at the respective temperatures were converted on the basis of the values obtained in the case of Bacillus sp. bacteria R332 being set to be 100, respectively. The converted values are shown in Table 3.

TABLE 3

| Reaction temperature (°C.) | Bacillus smithii SC-J05-1 | Bacillus sp. bacteria R332 |
|---|---|---|
| 30 | 275 | 100 |
| 40 | 675 | 100 |
| 50 | 5200 | 100 |
| 60 | 6200 | 100 |
|  | (present invention) | (control) |

EXAMPLE 4

Reaction Using Cultured Broth of Bacterial Cells

To 100 mL of the cultured broth of bacterial cells of *Bacillus smithii* SC-J05- 1 obtained in Example 3, was added 2.5 g (47.2 mmol) of acrylonitrile, and the reaction was effected at 20° C. while stirring with a magnetic stirrer. After 3 hours, 1.0 mL of the reaction mixture was taken, to which 0.1 mL of 2N HCl was added for stopping the reaction. This aliquot of the reaction mixture was analyzed by gas chromatography under the same conditions as described in Example 1. As a result, all the portions of acrylonitrile were entirely converted into acrylamide, and there were found no formation of by-products such as acrylic acid.

EXAMPLE 5

Reaction Using Bacterial Cells

From 150 mL of the cultured broth of bacterial cells of *Bacillus smithii* SC-J05-1 obtained in Example 3, the bacterial cells were collected by centrifugation at 10,000×g for 10 minutes. After washing with 0.05M phosphate buffer, pH 7.7, these bacterial cells were suspended in 50 mL of the same buffer. To this suspension was added 3.0 g (56.6 mmol) of acrylonitrile in three portions, and the reaction was effected at 20° C. while stirring with a magnetic stirrer. After 4 hours, 1.0 mL of the reaction mixture was taken, to which 0.1 mL of 2N HCl was added for stopping the reaction. This aliquot of the reaction mixture was analyzed by gas chromatography under the same conditions as described in Example 1. As a result, all the portions of acrylonitrile were entirely converted into acrylamide, and there was found no formation of by-products such as acrylic acid.

On the other hand, the bacterial cells were removed from the remaining reaction mixture by centrifugation at 10,000×g for 10 minutes, and the supernatant was concentrated by distillation below 50° C. to cause deposition of crystals, which were then recrystallized from methanol to give 3.7 g (52.1 mmol, 92% yield) of colorless plate-shaped crystals. Measurement of melting point, elementary analysis, IR spectra and NMR spectra confirmed that these crystals were acrylamide.

EXAMPLE 6

Reaction Using Enzyme Solution

From 8 L of the cultured broth of bacterial cells of *Bacillus smithii* SC-J05-1 obtained in Example 3, the bacterial cells were collected by centrifugation at 10,000×g for 10 minutes. After washing, these bacterial cells were suspended in 300 mL of 0.05M HEPES-KOH buffer, pH 7.2, and disrupted two times with a French press at 20,000 psi. The disrupted cells were centrifuged at 10,000×g for 30 minutes to remove the residual bacterial cells. Using a dialysis tubing (Wako Pure Chemical Industries, Ltd.), the supernatant was dialyzed against four changes of 10 mM HEPES-KOH buffer, pH 7.2, at 4° C. 24 hours. The dialysate was allowed to pass through a column (50 mmφ×200 mm) of DEAE-Sepharose FF (Pharmacia) as an anion exchange resin, previously equilibrated with 0.05M HEPES-KOH buffer, pH 7.2, thereby effecting adsorption of enzymes thereon.

Then, 0.05M HEPES-KOH buffer, pH 7.2, was allowed to pass through the column for washing, and elution was effected by a gradient of 0.05M HEPES-KOH buffer, pH 7.2, containing 0M to 1.0M potassium chloride. The fraction exhibiting the hydration activity to convert a nitrile compound into its corresponding amide compound was recovered and dialyzed using a dialysis tubing (Wako Pure Chemical Industries, Ltd.), against four changes of 10 mM HEPES-KOH buffer, pH 7.2, at 4° C. for 24 hours. The dialysate was purified by anion exchange chromatography under the same conditions as described above, except that elution was effected by a gradient of 0.05 mM HEPES-KOH buffer, pH 7.2, containing 0.2M to 0.8M potassium chloride. The eluent was dialyzed in the same manner as described above, which afforded a crude enzyme solution.

The activity to convert a nitrile compound into its corresponding amide compound was determined as follows:

First, 1 mL of the crude enzyme solution was added to 9 mL of 100 mM aqueous propionitrile, pH 7.7, and the reaction was initiated at 10° C. After ten minutes, 1 mL of 2N HCl was added for stopping the reaction. An aliquot of the reaction mixture was taken and analyzed by gas chromatography to determine the amount of propionamide produced.

With respect to the unit of enzyme activity as used hereinafter, the activity to convert 1 mmol of propionitrile into propionamide per minute was defined as one unit (U).

The crude enzyme solution thus obtained was diluted with 0.05M phosphate buffer, pH 7.7. To 100 mL of this dilution was added 2.5 g (47.2 mmol) of acrylonitrile, and the reaction was effected at 20° C. While stirring with a magnetic stirrer. After 3 hours, 1.0 mL of the reaction mixture was taken, to which 0.1 mL of 2N HCl was added for stopping the reaction. This aliquot of the reaction mixture was analyzed by gas chromatography under the same conditions as described in Example 1. As a result, all the portions of acrylonitrile added were entirely converted into acrylamide, and there was found no formation of by-products such as acrylic acid.

EXAMPLE 7

Conversion of Various Nitrile Compounds

In this example, nitrile-hydrating enzymes contained in *Bacillus smithii* SC-J 05-1 were examined for the ability to convert various nitrile compounds into their corresponding amide compounds. To 60 U of the crude enzyme solution obtained in Example 5, were added 20 mL of 0.05M phosphate buffer, pH 7.7, and 1 mmol of each of the tested nitrile compounds shown in Table 4 as a substrate, and the reaction was effected at 30° C. for 3 hours. As a result, it was found that the crude enzymes prepared from *Bacillus smithii* SC-J05-1 had hydration activity to convert all the tested nitrile compounds into their corresponding amide compounds. The reaction mixture was analyzed by gas chromatography or liquid chromatography to determine the amount of amide compound produced or the amount of nitrile compound consumed.

TABLE 4

| Tested nitrile compounds | |
|---|---|
| n-Butyronitrile | Malononitrile |
| n-Valeronitrile | Succinonitrile |
| Isobutyronitrile | Adiponitrile |
| 2-Chloropropionitrile | Acetonitrile |
| Acrylonitrile | Pivalonitrde |
| Crotononitrile | Methacrylonitrile |
| 3-Cyanopyridine | Benzonitrile |
| 4-Cyanopyridine | 2-Cyanopyridine |

According to the present invention, various nitrile compounds can be stably converted into their corresponding amide compounds even in the range of temperature higher than room temperature, which makes it possible to produce high-purity amide compounds with high efficiency over a wider temperature range as compared with the conventional processes which are usually conducted at low temperatures.

What is claimed is:

1. A process for production of amide compounds, which comprises converting a nitrile compound into its corresponding amide compound by hydrating said nitrile compound in the presence of a cultured broth of bacterial cells, intact bacterial cells, disrupted bacterial cells or enzymes contained therein, or immobilized preparations obtainable by immobilizing intact bacterial cells, disrupted bacterial cells or enzymes contained therein, said bacterial cells being cells of a biologically pure culture of a thermophilic microorganism *Bacillus smithii* SC-J05-1 (FERM BP-4935) having hydration activity to convert a nitrile compound into its corresponding amide compound.

2. A biologically pure culture of *Bacillus smithii* SC-J05-1 (FERM BP-4935) or a mutant thereof having hydration activity to convert a nitrile compound into its corresponding amide compound.

3. A process according to claim 1 wherein the concentration of said bacterial cells, disrupted bacterial cells or enzymes contained therein is 0.01 to 20% by weight.

4. A process according to claim 1 wherein the temperature of the hydration reaction is 0° to 70° C.

5. A process according to claim 1 wherein the pH of the hydration reaction is 6 to 9.

6. A process according to claim 1 wherein said nitrile is selected from the group consisting of n-butyronitrile, n-valeronitrile, isobutyronitrile, 2-chloropropionitrile, acrylonitrile, crotononitrile, 3-cyanopyridine, 4-cyanopyridine, malononitrile, succinonitrile, adiponitrile, acetonitrile, pivalonitrile, methacrylonitrile, benzonitrile and 2-cyanopyridine.

7. A process according to claim 1 wherein said nitrile is acrylonitrile and said amide is acrylamide.

8. A process according to claim 1 wherein said nitrile is propionitrile and said amide is propionamide.

9. A process according to claim 1 wherein said hydration of said nitrile is in the presence of an enzyme preparation from *Bacillus smithii* SC-J05-1 (FERM BP-4935).

* * * * *